(12) United States Patent
Geiler et al.

(10) Patent No.: US 6,927,853 B2
(45) Date of Patent: Aug. 9, 2005

(54) METHOD AND ARRANGEMENT FOR OPTICAL STRESS ANALYSIS OF SOLIDS

(75) Inventors: Hans-Dieter Geiler, Jena (DE); Matthias Wagner, Jena (DE)

(73) Assignee: Jena-Wave GmbH, Jena (DE)

( * ) Notice: Subject to any disclaimer, the term of this patent is extended or adjusted under 35 U.S.C. 154(b) by 340 days.

(21) Appl. No.: 10/280,709

(22) Filed: Oct. 25, 2002

(65) Prior Publication Data

US 2003/0081196 A1 May 1, 2003

(30) Foreign Application Priority Data

Oct. 28, 2001 (DE) .......................................... 101 54 008

(51) Int. Cl.$^7$ .......................... G01B 11/16; G01N 21/21
(52) U.S. Cl. .......................... 356/367; 356/33; 356/368
(58) Field of Search ................... 356/33–35, 364–370; 250/225

(56) References Cited

U.S. PATENT DOCUMENTS

| | | | |
|---|---|---|---|
| 4,629,323 A | | 12/1986 | Matsumoto |
| 5,247,176 A | | 9/1993 | Goldstein |
| 5,521,705 A | | 5/1996 | Oldenbourg et al. |
| 5,648,850 A | * | 7/1997 | Basler et al. ............... 356/369 |
| 6,055,053 A | * | 4/2000 | Lesniak ..................... 356/366 |
| 6,665,059 B2 | * | 12/2003 | Kanno et al. ................ 356/33 |
| 2001/0028451 A1 | | 10/2001 | Kanno et al. |

FOREIGN PATENT DOCUMENTS

| | | |
|---|---|---|
| DE | 31 29 505 | 6/1982 |
| DE | 36 44 705 | 7/1987 |
| DE | 42 11 742 | 10/1992 |
| DE | 195 11 707 | 10/1996 |
| WO | WO 98/55844 | 12/1998 |

OTHER PUBLICATIONS

*Experimental Stress Analysis*, McGraw–Hill, New York 1991, J. W. Dally and W. F. Riley, Chapter 12, "Theory of Photoelasticity" pp. 424–505.

Opt. Lett. 2 (6) (1978): R. M. A. Azzam "Photopolarimetric measurement of the Mueller matrix by Fourier of a single detected signal" pp. 148–150.

\* cited by examiner

*Primary Examiner*—Richard A. Rosenberger
(74) *Attorney, Agent, or Firm*—Reed Smith LLP

(57) ABSTRACT

A method for optical stress analysis comprises the steps of directing an incident beam of polarized light to the sample to be analyzed and analyzing a light bundle exiting the sample in two detection channels extending perpendicular to one another with respect to the polarization direction, providing that the incident beam is elliptically polarized, carrying out the elliptical polarization with an elliptic shape having a comparatively large ratio of the large principal axis to the small principal axis, the direction of rotation of the elliptical polarization of the incident beam changing periodically and using two alternative states of the direction of rotation for each measurement process, adjusting the detection channels which extend perpendicular to one another corresponding to the position of the principal axes of the ellipse and carrying out the difference between two measurements consecutively with the same beam intensity of the incident beam and the same ratio of principal axes, but with opposite direction of rotations of the elliptical polarization, being given by the two detection channels. An arrangement in accordance with the method is also disclosed.

15 Claims, 6 Drawing Sheets

METHOD AND ARRANGEMENT FOR OPTICAL STRESS ANALYSIS OF SOLIDS

CROSS-REFERENCE TO RELATED APPLICATIONS

This application claims priority of German Application No. 101 54 008.6, filed Oct. 28, 2001, the complete disclosure of which is hereby incorporated by reference.

BACKGROUND OF THE INVENTION a) Field of the Invention

The invention is directed to a method and an arrangement for optical stress analysis of solids based on the measurement of the change in the polarization state of light passing through material.

b) Description of the Related Art

In the field of material testing for absence of stress, polarimetric measurement of stress in the test piece by means of a quantity proportional to the shearing stress has proven desirable. However, the real problem with these methods, known per se, consists in that the quantity to be measured is given by typically extremely small phase shifts ($\Gamma < 10^{-4}$) between the ordinary and extraordinary beam. In this connection, it is self-evident that such small measurement quantities are subject to a variety of disturbances that can have an unwanted influence on measurements and must therefore be suitably suppressed. Further, economically sensible evaluation of test pieces in a production process requires measurement times which are on the order of magnitude of the process cycle time, that is, as short as possible. Therefore, known technical solutions must be gauged based on the extent to which they can simultaneously satisfy the three conditions mentioned above.

The use and construction of polarimeters for detecting stress states in plates by utilizing the effect of stress induced birefringence have been described many times in the literature. A general survey of the methods currently being used is presented in J. W. Dally and W. F. Riley [*Experimental Stress Analysis*, McGraw-Hill, New York 1991: 424–505].

The known concepts and practical implementation of simple basic constructions of polarimeters are also shown in DE 31 29 505 A1 and DE 36 44 705 C2.

In DE 31 29 505 A1, monochromatic, circularly polarized light is passed through the test piece in a known manner and the change in this polarization state is detected as light power I by an analyzer combination comprising a λ/4 plate and a Wollaston prism, over two light output channels by means of photocells. This method gives phase shift $\Gamma$ by means of the equation $\tan^2\Gamma = I_1/I_2$, where $I_1$ and $I_2$ are the intensities of the two light output channels. It will be seen immediately that these methods do not provide directional information about the position of the principal axes of elliptically polarized light and provide exclusively a quadratic dependence of the phase shift. Due to the quadratic dependence, the sensitivity approaches zero particularly for small phase shifts $\Gamma$ and statistically equally distributed depolarizations in the material lead to erroneous measurement results in the direction of high values of the phase shift.

This lack of directional information is overcome in Patent DE 36 44 705 C2 in that linearly polarized light is used and the angle between the principal axes of index ellipsoid of the sample and the polarization direction is varied by mechanically moving elements. In a modification and expansion of the principle described in DE 36 44 705 C2, measurement methods which carry out the measurement with two linear polarization directions rotated by 45° or 90° are also known (U.S. Pat. Nos. 4,629,323; 5,521,705). However, none of these methods is capable of overcoming the disadvantages resulting from the quadratic dependence, namely, an extremely low measurement sensitivity for small phase shifts and a falsification of the measurement results in the direction of high values brought about by depolarizations which are statistically equally distributed in the material.

Another basic approach is presented by concepts which attempt to directly determine the elements of the Mueller matrix (R. M. A. Azzam, *Opt. Lett.* 2 (6) (1978): 148]. Known practical implementations are arranged as two-channel polarimeters in which the change in intensity of a linearly polarized light beam is detected after interaction with the sample in two receiver channels with orthogonal analysis.

A solution disclosed in U.S. Pat. No. 5,247,176 has two phase delays (retarders) which rotate synchronously at different speeds. Apart from the use of two retarders, this solution requires an extremely high optical-mechanical precision of the rotating apparatus and considerable numeric calculation because the measurement results are obtained from a Fourier analysis of the measurement signals. Although the method does not have a vanishing measurement sensitivity even with small phase shifts (around $\Gamma = 0$), accuracy is limited due to the fact that higher order Fourier coefficients have great weight in the measurement results. The accurate determination of such coefficients requires a precisely synchronized and uniform rotation of the two retarders and is therefore very complicated and time-consuming.

The suitability of the solution described in DE 42 11 742 A1 depends on the exact mutual mechanical adjustment of a plurality of polarization-selective component groups which are arranged one behind the other. The quality of this adjustment directly determines the measurement sensitivity and measurement accuracy of the arrangement. This means that expenditure on adjustment rises sharply particularly for the measurement of small phase shifts (around $\Gamma = 0$). Moreover, this solution is unsuitable in principle for the suppression of statistically equally distributed depolarizations in the measurement sample.

Therefore, none of the prior art solutions are capable of achieving at a reasonable expenditure a high measurement sensitivity for small phase shifts (around $\Gamma = 0$) with depolarizations directed in a defined manner due to stress birefringence and, simultaneously, a suppression of depolarisation which are statistically eqally distributed in the measurement sample.

OBJECT AND SUMMARY OF THE INVENTION

It is the primary object of the invention to find a novel possibility for measurement of stresses in solids based on stress induced birefringence which enables a highly-sensitive quantitative determination of the phase difference (between the ordinary and extraordinary beam) particularly for small changes in the polarization state with extensive suppression of statistically equally distributed disturbance influences (e.g. scattering) in the measurement results.

According to the invention, in a method for optical stress analysis in which an incident beam of polarized light is directed to the sample to be analysed and a light bundle exiting the sample is analysed in two detection channels extending perpendicular to one another with respect to the polarization direction, the above-stated object is met in that the incident beam is elliptically polarized, the elliptical polarization being carried out with an elliptic shape having a comparatively large ratio of the large principal axis to the small principal axis, meaning a small latitude angle (ellipticity), in that the direction of rotation of the elliptical polarization (sign of the latitude angle) of the incident beam changes periodically while the longitude angle (azimuth angle of the large principal axis) remains constant, wherein two alternative states of the direction of rotation are used for each measurement process, in that the detection channels which extend perpendicular to one another are adjusted corresponding to the position of the principal axes of the ellipse exactly according to the longitude angle with the latitude angle of zero (linear polarization) which is preselected for the adjustment, and in that the difference and sum between two measurements carried out consecutively with the same beam intensity of the incident beam and the same ratio of principal axes, but with opposite directions of rotation of the elliptical polarization, is given by the two detection channels.

In an advantageous manner, the elliptical polarization can be generated in that the beam incident on the sample is initially linearly polarized, the two detection channels also being exactly oriented parallel to and perpendicular to the incident beam, and subsequently passes through a birefringent phase retardation plate, wherein the ratio of the principal axes and the direction of rotation of the elliptical polarization are adjusted by the mutual orientation of the spatial position of the linear polarization to the principal axes of the phase retardation plate. In addition, in the measurements used for giving the difference, the angular position of the fast principal axis of the retardation plate changes in such a way that the direction of rotation of the elliptical polarization reverses while the ratio of the principal axes of the elliptical polarization (tangent of the latitude angle) remains unchanged.

Another advisable variant for generating the elliptical polarization consists in that the incident beam is likewise linearly polarized before the sample and passes a controllable phase modulator, wherein the ratio of principal axes and the direction of rotation of the elliptical polarization are adjusted by control signals of the phase modulator. The control signals of the phase modulator are periodically modulated in such a way that an elliptical polarization occurs with periodically changing direction of rotation, and the evaluation of the difference between successive measurements is carried out by means of a lock-in detector which is synchronously clocked by the control signal of the phase modulator.

A linearly polarized laser beam is preferably used for realizing a linearly polarized incident beam.

The incident beam is advisably modulated in intensity and the measurement values of the detection channels are detected by modulation-synchronous lock-in detectors in order to measure the very small stress-dependent phase shifts of the polarization with low noise.

The essential features of the method according to the invention will be described in the following with reference to a mathematical-physical description.

Let the measured sample be characterized by the phase difference $2\Gamma$ which is generated by its birefringence between the ordinary (o) and extraordinary (e) beam:

$$\Gamma = \frac{\pi d}{\lambda}(n_e - n_o),$$

where $n_e$, $n_o$ are the principal refractive indices of the material, d is the thickness of the test piece, and $\lambda$ is the wavelength of the light.

Let the angle between the E-field vector of the linearly polarized light and fast axis of the (at least locally) birefringent measurement sample be designated by $\gamma$. Let the retarder be described by the same formalism and its phase shift be designated by $\Lambda$ and the angle between the E-field vector and the fast axis by $\rho$.

Let $I_{\parallel}$ and $I_{\perp}$ designate the normalized light intensities on the light receivers detecting the polarized light parallel and perpendicular to the orientation of the linear polarizer, then (with an intensity $I_{\parallel}+I_{\perp}=1$ normalized to one) the following is given for the perpendicular oriented channel:

$$I_{\perp} = \sin^2\Gamma \cdot \sin^2\Lambda \cdot [\sin^2 2(\gamma - \rho) - \sin^2 2\gamma - \sin^2 2\rho] +$$
$$\sin^2\Gamma \cdot \sin^2 2\gamma + \sin^2\Lambda \cdot \sin^2 2\rho +$$
$$\frac{1}{2}\sin 2\Lambda \sin 2\rho \cdot \sin 2\Gamma \sin 2\gamma$$

The change in the states of the direction of rotation is described by the reversal of the sign of $\Lambda$ (electro-optic control possibility) or by the transition $\rho \rightarrow \rho \pm 90°$ (mechanical control possibility). It will be seen that for measurements separated in time in two measurement phases A and B which differ by the sign of $\Lambda$ or by the 90° angle of $\rho$, only the last term of the sum contributes to the measurement results of the perpendicular channel.

Let $I_{\perp_A}$ and $I_{\perp_B}$ represent the measured normalized intensities in the measurement phases A and B, then the measurement results can be calculated as $\Delta I_{\perp}=I_{\perp_A}-I_{\perp_B}$, and:

$$\Delta I_{\perp}=\sin 2\Lambda \sin 2\rho \cdot \sin 2\Gamma \sin 2\gamma$$

For small phase shifts $\Gamma$, this is directly proportional to the local shear stress $\tau$ in the measurement sample:

$$\Delta I_{\perp} \approx 2\Gamma \sin 2\gamma \sim \tau.$$

It can be seen that the above mathematical description is invariant with regard to a transposition of the variable pairs $\Gamma$, $\gamma$ and $\Lambda$, $\rho$. This means that the positions of the retarder and of the measurement sample in the beam path can be exchanged.

Further, in an arrangement for optical stress analysis of materials based on stress induced birefringence in which a light source is provided for generating a polarized beam incident on a sample to be analyzed and a polarizing splitter is provided for dividing a light bundle exiting from the sample into two light receivers for detecting polarization directions perpendicular to one another, the object of the invention is met in that an optical unit is provided for generating elliptically polarized light with adjustable ratio of the principal axes of the elliptical polarization, wherein the direction of rotation of the elliptical polarization is adjustable in opposite directions with the ratio of the principal axes remaining constant, in that the polarizing splitter acting as analyzer is oriented corresponding to the position of the principal axes of the ellipse (longitude angle) for the polarization directions extending perpendicular to one another, in that an electronic control unit is provided for synchronizing and allocating the intensity values of the two light receivers to the states of the direction of rotation that are adjusted by means of the optical unit, and in that a processing unit is provided for evaluating the intensity values of the two light receivers for two associated states with opposite directions of rotation, the intensity values of the one light receiver which are measured for associated states are subtracted and this difference is normalized to the sum of the intensity values of both light receivers for both associated states.

A controllable optical phase shifter (hereinafter: retarder) which is arranged in the optical light path between the light source and the polarizing splitter is preferably used as an optical unit for adjusting two states of opposite directions of rotation.

The optical unit can advantageously have a mechanically controlled retarder which has a changeable angular position or an electronically controllable optical phase modulator which has an alternating phase delay.

An electro-optical or magneto-optical phase modulator can be used as optical phase modulator, wherein the phase delay is adjustable by changing the control voltage or the control current.

Particularly suitable embodiment forms are those with electronic phase shifters or polarization rotators which contain no mechanically moving optical parts and therefore have high measuring speed and precision so that they can be used for systematic point-by-point scanning of large-area measurement samples.

The basic idea of the invention is to change an arrangement, known per se, for polarization analysis through additional structural component parts in such a way that the light used for analyzing the measurement sample is polarized in a strongly elliptical manner (with a small latitude angle, i.e., with a comparatively large ratio of the large principal axis to the small principal axis) rather than linearly as was conventional. As a result of using light which is polarized elliptically in this way, the intensity on the light receiver receiving that proportion of light whose oscillation direction corresponds to the direction of the small principal axis of the elliptical polarization depends linearly, rather than quadratically, upon the phase shift of the light in the measurement sample for weak birefringence of the measurement sample. This ensures an extreme increase in measuring sensitivity for small phase shifts. In order to obtain measurements which can be evaluated quantitatively, measurement values are taken in two different states (measurement phases A and B) which are characterized in that the states of the directions of rotation of the elliptical polarization are opposite in measurement phases A and B while the ratio of principal axes remains constant. The result is obtained by taking the difference of the intensity values from phases A and B. This subtraction can be carried out by sequential individual measurements in measurement phases A and B followed by numeric data processing, as well as by means of modulation of the direction of rotation of the elliptical polarization periodically with respect to time, combined with one of the known phase-synchronous detection techniques (e.g., lock-in detection). In this way, the changes in the polarization state (depolarization through signed phase shift in the material) caused by the stress-dependent birefringence can be isolated from disturbance components such as those occurring due to statistical depolarizing scatter in the material (non-signed depolarization effects).

Further, based on the fundamental ideas of the invention, the measuring sensitivity of the apparatus can be adjusted within broad limits when the ratio of the principal axes of the elliptical polarization is arranged so as to be variably adjustable.

In addition, calibration measurements are useful for quantifying the results:

(1) Calibration of the zero point. Due to the technical deficiencies of every real system, asymmetries occur between the measurement phases A and B so that $I_{\perp_A} \neq I_{\perp_B}$ even without the measurement sample, and these asymmetries must be compensated by zero balancing. For this purpose, a measurement must be taken without the measurement sample ($\Gamma=0$). Balancing the values $\Lambda$ and $\rho$ of the two measurement phases A and B produces $\Delta I_\perp = 0$.

(2) Calibration of measurement sensitivity. The measurement sensitivity is determined by the quantity $K = \sin 2\Lambda \sin 2\rho$. This quantity is determined by carrying out an additional measurement without the measurement sample ($\Gamma=0$), for example, in the state of measurement phase A. At least one of the two quantities $\Lambda$ or $\rho$ of the retarder is always known. In the case of a retardation plate, this is generally $\Lambda$; in the case of an optical phase modulator it is generally $\rho$. The air measurement (without measurement sample) gives the value $I_{\perp_A} = \sin^2 \Lambda \sin^2 2\rho$, from which K can be determined.

(3) Normalizing the intensity. The sum of the signal powers in the two measurement phases A and B must be determined for normalizing the measurement values $S_{\perp_A}$, $S_{\perp_B}$, $S_{\|A}$ and $S_{\|B}$ obtained at the lock-in detector in order to determine intensity $\Delta I_\perp$. The normalized intensity $\Delta I_\perp$ introduced in the mathematical description above is then determined as $$\Delta I_\perp = 2(S_{\perp_A} - S_{\perp_B})/(S_{\|A} + S_{\perp_A} + S_{\|B} + S_{\perp_B}).$$

Since at least the intensities to be measured in the perpendicular polarized detection channel are very small because of the small ratio of the principal axes of the elliptical polarization, the intensity measurement of the two detection channels is preferably carried out by modulating the light source and lock-in detection (corresponding to the generally known technique for detecting small light intensities).

In the case of a retarder with changeable angle orientation, the analysis of the optical stress characteristics over a surface of the measurement sample is carried out by scanning the surface twice with different angle orientation and subsequently subtracting the two measurement data associated with a measurement point. When using an electro-optical or magneto-optical phase modulator, the analysis of the optical stress characteristics along a surface can be carried out by scanning the surface and recording the output signal of the lock-in detector which is used for the subtraction of the intensity values of the perpendicular polarized detection channel from phases A and B.

The method and the arrangements according to the invention enable the measurement of stresses in solids based on stress birefringence which, particularly for small changes in the polarization state, achieves a highly sensitive quantitative determination of phase differences with extensive suppression of statistically equally distributed interfering influences (e.g., scatter) on the measurement results.

The invention will be described more fully in the following with reference to embodiment examples.

DESCRIPTION OF THE PREFERRED EMBODIMENTS

Figure 1:
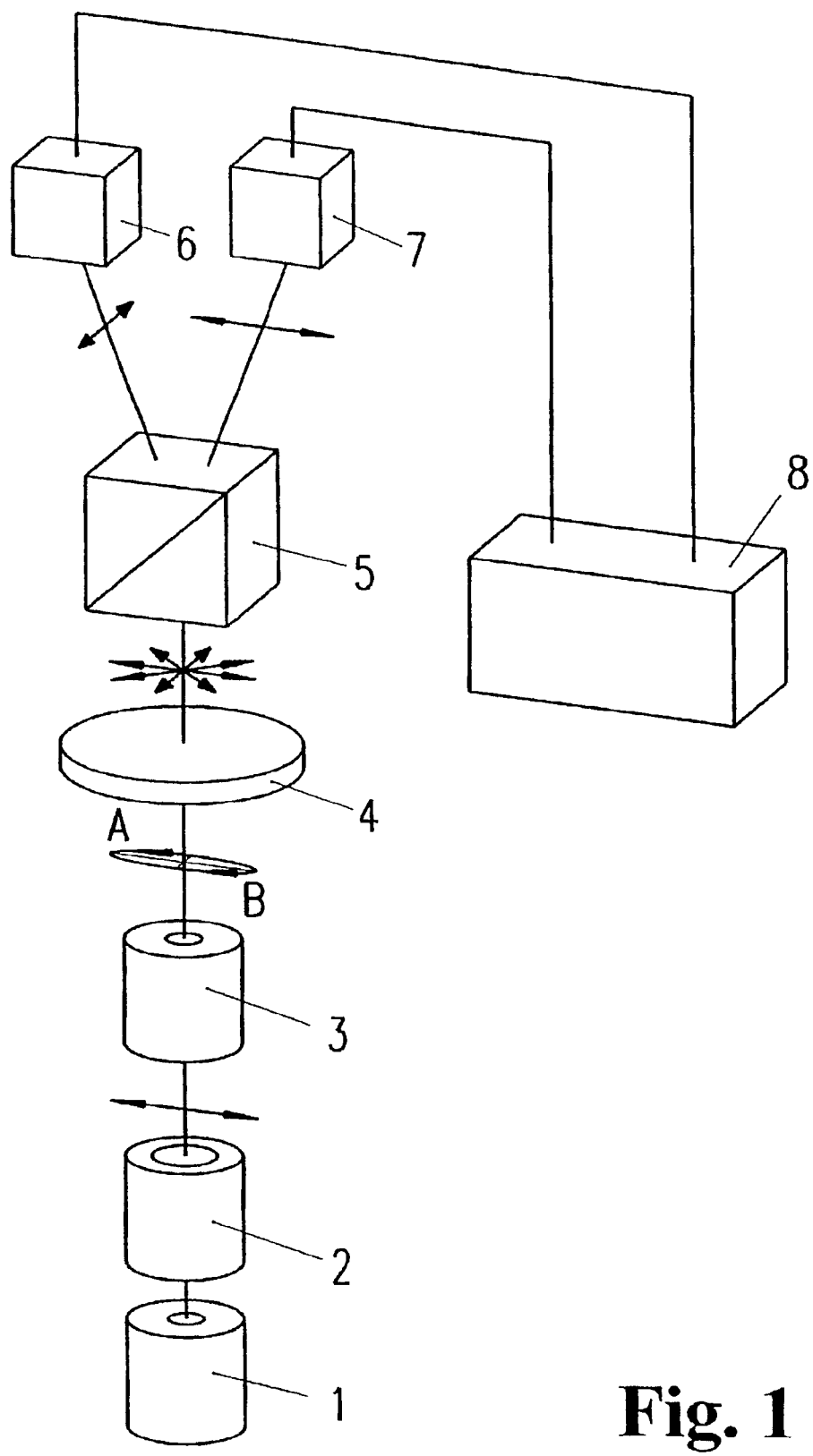
FIG. 1 shows schematically the method according to the invention for optical stress analysis in a transmission arrangement.

The method according to the invention and the arrangements based on the method rely on basic constructions of two-channel polarimeters, known per se, using linearly polarized light for analyzing phase shifts (birefringence effects). Known arrangements of this kind comprising, successively, a light source, a linear polarizer, the measurement sample, a polarizing splitter, one of whose two orthogonal polarization directions is oriented at 90° to the linear input polarization, and two light receivers measuring incident light intensities in two orthogonal polarization channels, are expanded, according to the invention, by an optical unit which produces an elliptical polarization of light. The elliptical polarization has the particular feature that the polarization ellipse has a very large ratio of the large principal axis to the small principal axis and, in two measurement phases A and B, a first state of the direction of rotation of the elliptical polarization can be switched to a second state with the opposite direction of rotation. This step can be achieved on the one hand by changing the ratio of the principal axes and on the other hand by changing the direction of the incident linear polarization. An optical unit, known per se, by means of which these requirements can be implemented is a phase-retarding device (known to the person skilled in the art as a retarder). For the novel purpose according to the invention, a retarder of this kind can be constructed so as to be controllable in different ways in principle:

a) alternating angle orientation of the retarder (mechanically controlled retarder);

b) alternating phase retardation of the retarder (electro-optical or magneto-optical phase modulator with alternating control voltage or control current).

Persons with skill in the field of polarization optics will be familiar with additional techniques.

In case (a), due to the comparatively slow movement speeds of the necessary mechanical adjusting elements, the difference is given by sequential individual measurement and subsequent numerical subtraction of the measured values.

In case (b), on the other hand, due to the high settling speeds of electro-optical components, the change in the direction of rotation of the elliptical polarization is carried out in the form of a modulation technique, so that the difference signal can be formed by means of the known technique of lock-in detection with the modulation frequency as reference clock, which allows a considerable increase in the measurement speed up to real-time capability.

In the arrangement shown schematically in FIG. 1, with reference to which the method according to the invention will be described initially, a beam of linearly polarized light is generated by means of a laser source 1 and a polarizer 2.

It passes the optical phase shifter 3 which generates a path difference that is comparatively small relative to the wavelength of the laser light (typically $\lambda/10 \ldots \lambda/1000$. The light exiting the optical phase shifter 3 is accordingly elliptically polarized with a comparatively large ratio of the large ellipse axis to the small ellipse axis. The optical phase shifter 3 has the characteristic that the direction of rotation of the elliptical polarization and the ratio of the axes can be controlled—as will be described more fully later on in the specific embodiment forms—in order to divide the measurement of the optical stress state into the two measurement phases A and B. The measurement phases A and B differ in that the direction of rotation of the elliptical polarization is reversed in the transition into the other respective phase, as is made clear in FIG. 1 by the different arrow directions at the polarization ellipse for measurement phases A and B.

After the elliptical polarization has been impressed on the beam impinging on the measurement sample 4, the beam suffers disturbance of its polarization state characteristic of the (local) stress state in the measurement sample 4 when penetrating the measurement sample 4. A polarizing splitter 5 divides a light bundle exiting the measurement sample 4 into two linearly polarized components whose intensities $I_\perp$ and $I_\parallel$ are measured by the light receivers 6 (channel of perpendicular polarization) and 7 (channel of parallel polarization). The associated photocurrents $S_\perp$ and $S_\parallel$ obtained from the light receivers 6 and 7 are registered in the processing unit 8 and processed as a function of the control state of the optical phase shifter 3.

Figure 2:
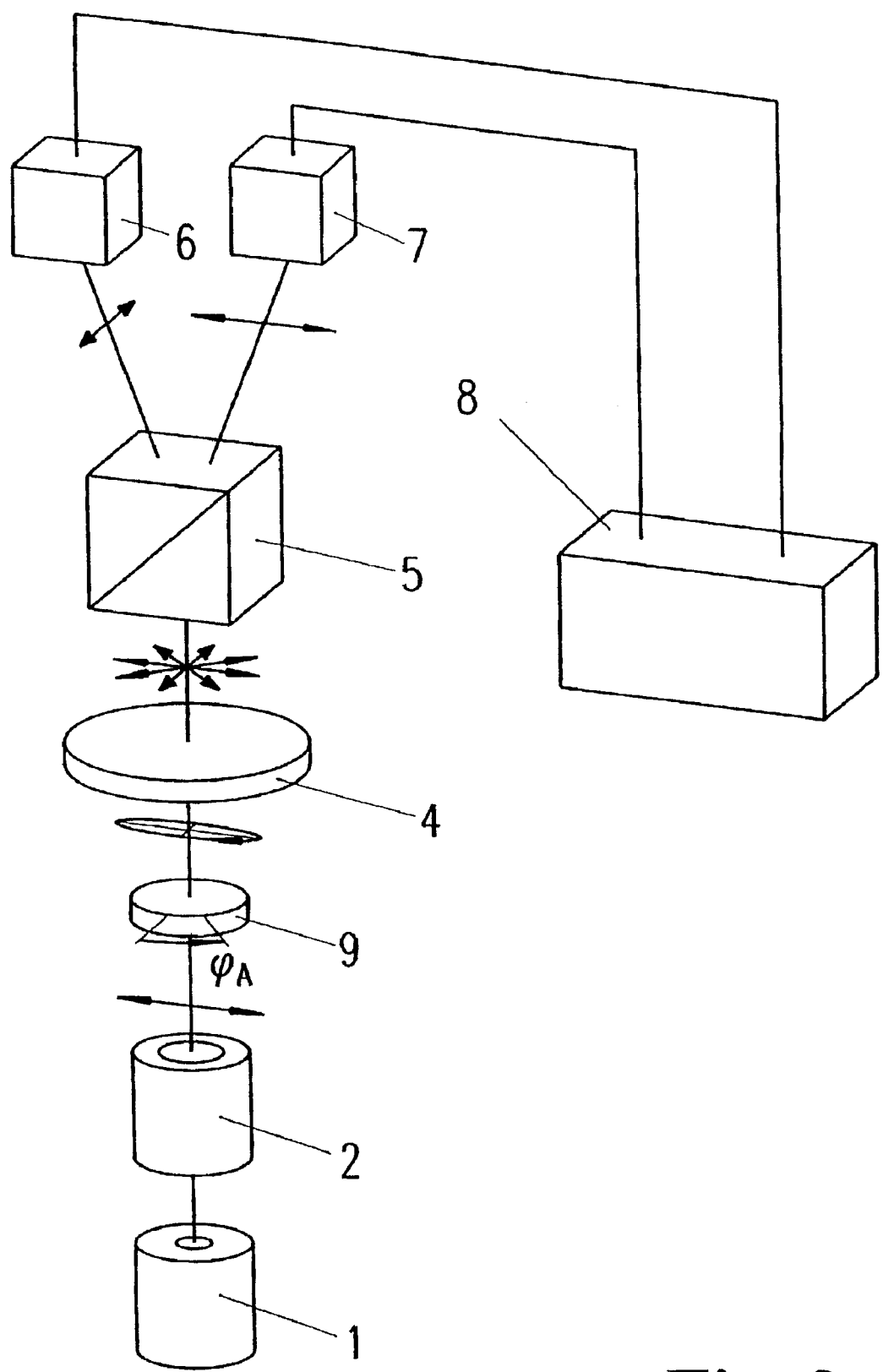
FIG. 2 shows an embodiment of an arrangement according to the invention with a birefringent phase retardation plate with adjustable orientation in a first measurement phase A.
Figure 3:
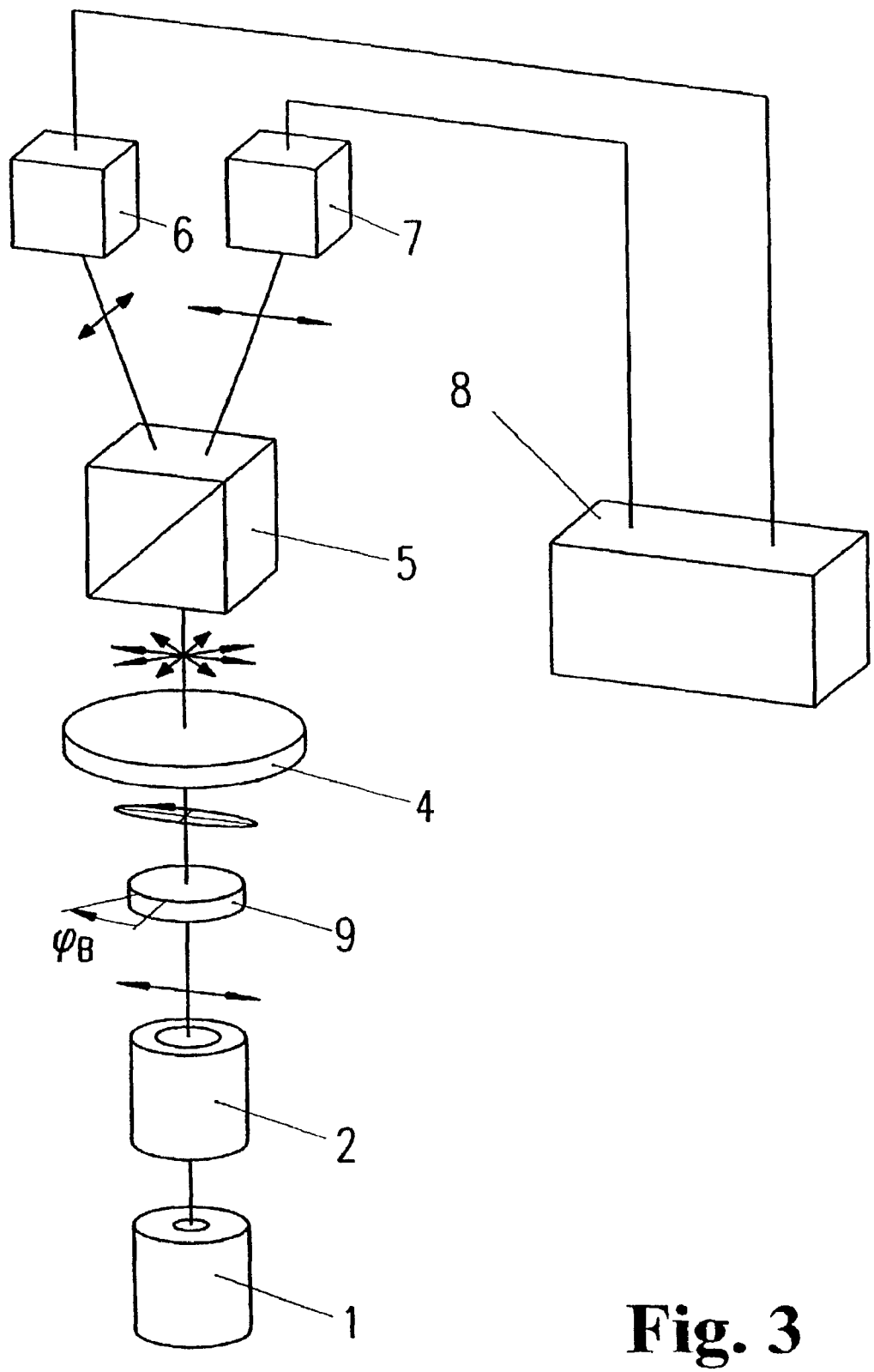
FIG. 3 shows the same embodiment form as in FIG. 1, but in a second measurement phase B.

FIGS. 2 and 3 show implementations of the method according to the invention in a transmission arrangement, wherein the controllable phase shifter 3 shown in FIG. 1 is realized by a birefringent phase retardation plate 9 with adjustable orientation. The position of the phase retardation plate 9 is shown in phase A (FIG. 2) and in phase B (FIG. 3) of a measurement for determining the stress state.

The measurement phase A shown in FIG. 2 is characterized in that the phase retardation plate 9 is rotated by angle $\phi_A$ relative to the polarization direction of the entering linearly polarized light (shown by the double arrow). The phase shift of the phase retardation plate 9 is in the range of $\lambda/1- \ldots \lambda/1000$, angle $\phi_A$ is in the range of $0 \ldots 45°$. The resulting direction of rotation of the polarization ellipse is marked by an arrow at the ellipse.

The measurement phase 3 in FIG. 3 shows that the phase retardation plate 9 is rotated by angle $\phi_B$ relative to the polarization direction of the entering linearly polarized light, where $\phi_B=\phi_A+90°$. The resulting direction of rotation of the polarisation ellipse is again identified by an arrow at the ellipse.

The measurement device 8 receives and amplifies the photocurrents obtained from the light receivers 6 and 7 in the same manner as in FIGS. 2 and 3.

When the light of the laser source 1 is intensity-modulated for improved suppression of extraneous light influences, which can be carried out by means of any chopper arrangement or by direct modulation of the laser source 1, the measurement device 8 advisably comprises two lock-in amplifiers (also known as lock-in detectors).

The measurement device 8 processes the photocurrents of the light receivers 6 and 7 in the following manner:

1. The photocurrents of the light receivers 6 and 7 are measured during the rotation of the phase retardation plate 9 by angle $\phi_A$. The measurement values $S_{\perp_A}$ and $S_{\parallel A}$ are measured;

2. The photocurrents of the light receivers 6 and 7 are measured during the rotation of the phase retardation plate 9 by angle $\phi_B$. The measurement values $S_{\perp_B}$ and $S_{\parallel_B}$ are measured;

3. The measurement values $S_{\perp_A}$, $S_{\parallel_A}$ and $S_{\perp_B}$, $S_{\parallel_B}$ of the light receivers 6 and 7 are normalized with respect to the intensities $I_\perp$ and $I_\parallel$ such that $$I_\parallel + I_\perp = 1;$$

4. The measured values are subtracted according to $$\Delta I_\perp = I_{\perp_A} - I_{\perp_B}.$$

In the arrangement according to FIGS. 2 and 3, the zero balancing is carried out in that, with the measurement sample 4 removed from the measuring arrangement, one of the two angles $\phi_A$ or $\phi_B$ is changed slightly relative to the condition $\phi_B = \phi_A + 90°$, which applies to an ideal system, until $\Delta I_\perp$ is sufficiently close to zero.

Figure 4:
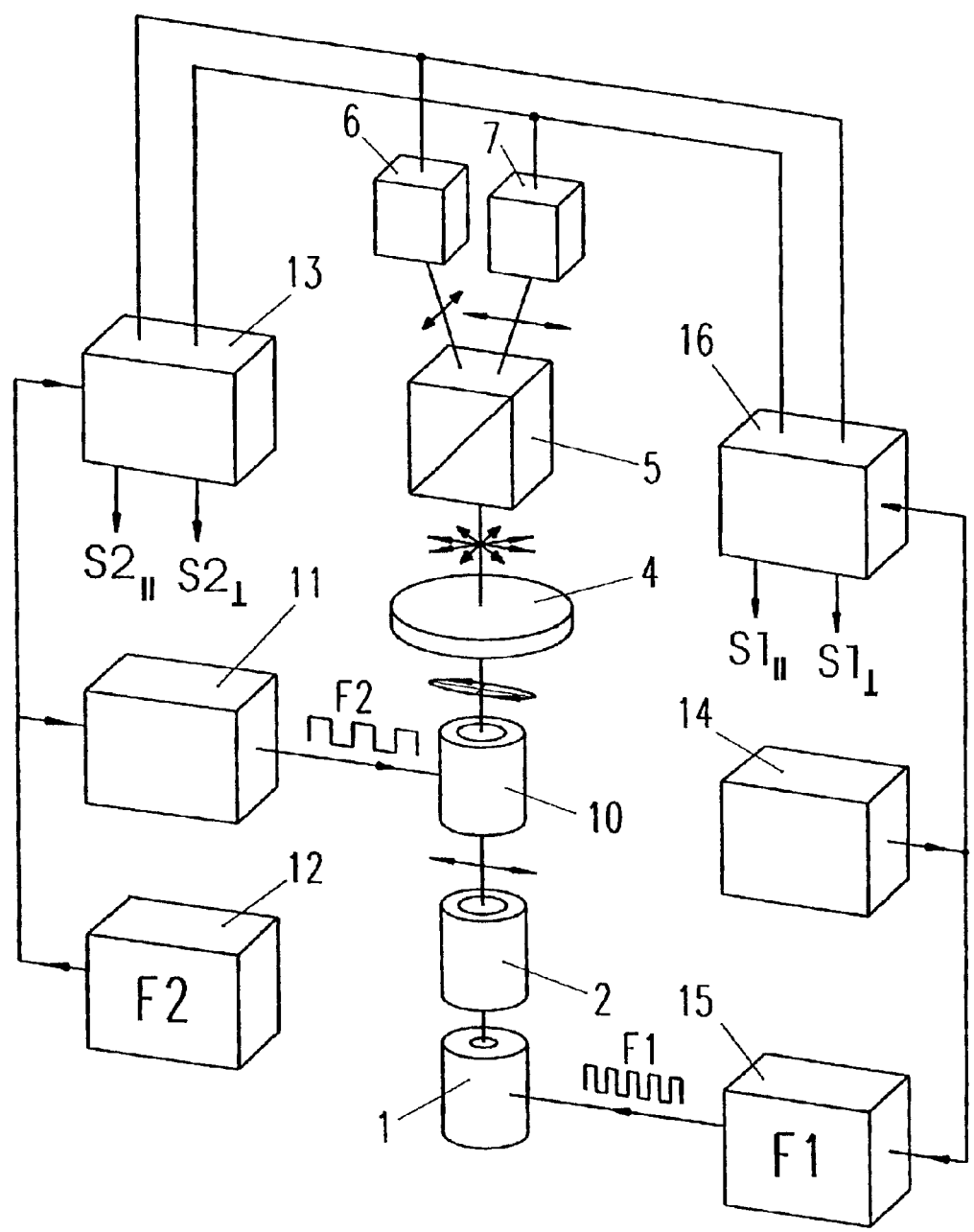
FIG. 4 shows the invention implemented in a transmission arrangement with an electro-optical phase modulator instead of the controllable phase shifter shown in FIG. 1.

In FIG. 4, the method according to the invention is realized in a transmission arrangement in which the controllable phase shifter 3 shown in FIG. 1 is implemented by means of an electro-optical phase modulator 10. The light source 1 is controlled by a modulator 15 which is clocked by an intensity clock generator 14 with frequency $F_1$. The electro-optical phase shifter 10 is controlled by a control voltage generator 11 which is clocked by a phase shifter clock generator 12 with frequency $F_2$. The electro-optical phase modulator 10 is oriented at $\rho = 45°$ in the beam path, so that the reversal of its control voltage leads to a sign reversal of its phase shift $\Lambda$. The phase shift $\Lambda$ generated by the control of the phase modulator 10 is typically in the range of $\lambda/10 \ldots \lambda/1000$.

The signals proceed from the light receivers 6 and 7 (measurement values $S_{\perp_A}$ and $S_{\perp_B}$; $S_{\parallel_A}$ and $S_{\parallel_B}$) to a two-channel lock-in detector 16 which detects the signal sum from $S_{\parallel_A}$, $S_{\perp_A}$, $S_{\parallel_B}$ and $S_{\perp_B}$ required for normalizing. The lock-in detector 16 receives its reference signal with frequency $F_1$ from the intensity clock generator 14.

Further, the signals proceed from light receiver 6 ($S_{\perp_A}$ and $S_{\perp_B}$) to another lock-in amplifier 13 which obtains its reference signal with frequency $F_2$ from the phase shifter clock generator 12.

Figure 5:
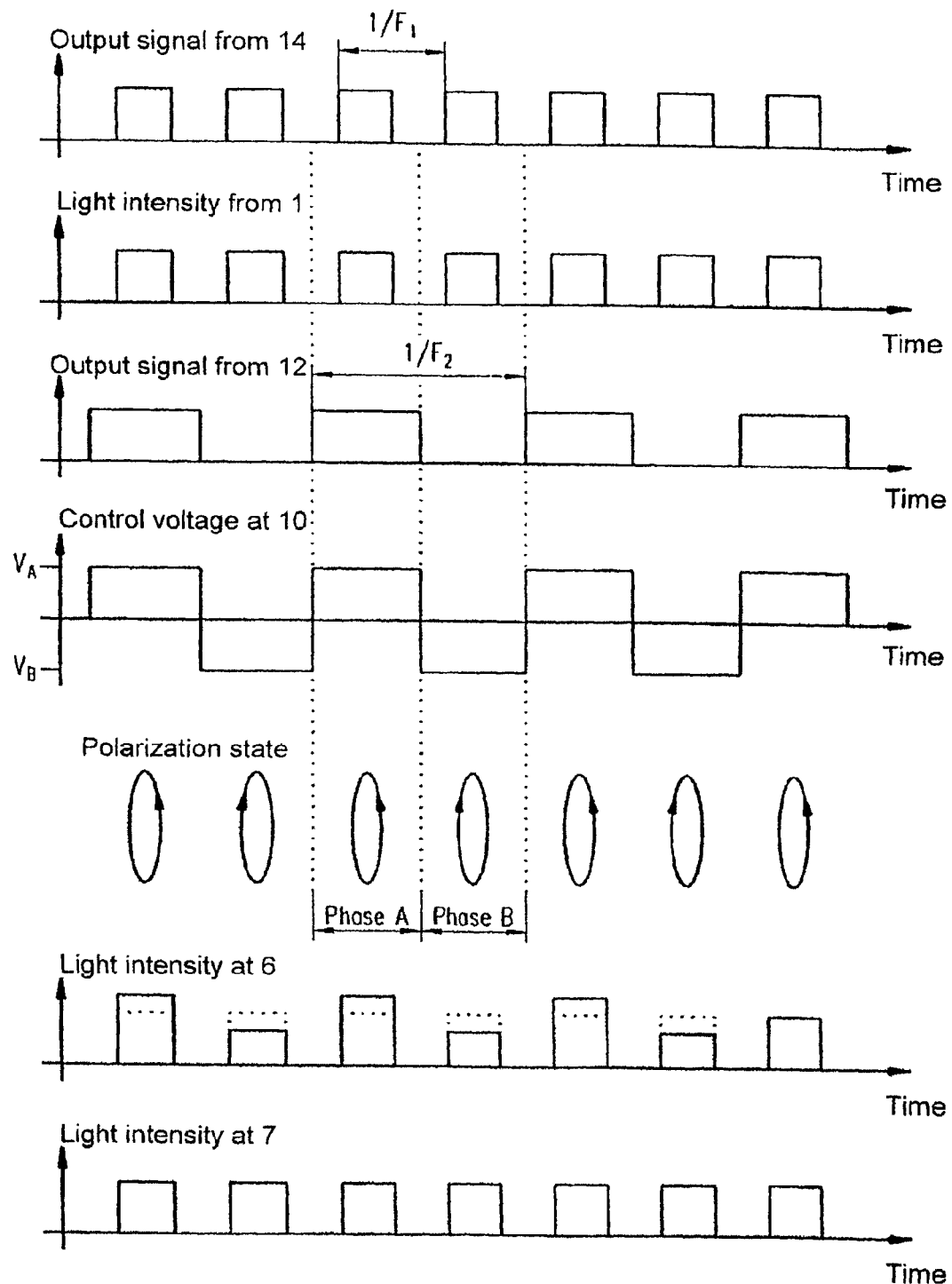
FIG. 5 shows the time chart of some signal shapes of the measurement arrangement for advantageous frequency selection $F_1=2F_2$.

A particularly advantageous implementation results by selecting $F_1 = 2F_2$. For this case, FIG. 5 shows time charts of some signals of the measurement arrangement. FIG. 5 shows, from top to bottom:

the output signal of the intensity clock generator 14 with frequency $F_1$;

the light intensity of the light source 1;

the output signal of the phase shifter clock generator 12 with frequency $F_2$;

the control voltage generated by control voltage generator 11 and applied to the phase modulator 10, wherein the control voltages applied to the phase modulator 10 in measurement phases A and B are designated by $V_A$ and $V_B$, respectively;

the polarization state of the light which exits from the phase modulator 10 and enters the measurement sample 4;

the intensity $I_\perp$ measured at the light receiver 6 when a sample is located in the beam path (solid line) and when no sample is located in the beam path (dashed line); and the intensity $I_\parallel$ measured at the light receiver 7.

When selecting the time functions for the control frequencies $F_1$ and $F_2$, it is particularly advantageous to set the switching moment for the control voltage for the phase modulator in the OFF state of the light source, since in that case the always finite changeover time period, i.e. the finite switching velocity, causes minimal disturbance of the measurement results.

As can be seen from the time charts, the lock-in detection of the output signals of the light receivers 6 and 7 with reference frequency $F_1$, according to the invention, supplies the arithmetic averages of the measurement signals $S_\perp$ and $S_\parallel$ from the time segments A and B which are required for normalizing the intensity values. The detection of the output signal of the light receiver 6 with reference frequency $F_2$ supplies the value $\Delta I_\perp \cdot N$, where N is the normalization constant.

In the arrangement according to FIG. 4, the zero balancing is carried out in that, with the measurement sample removed from the measuring arrangement, one of the two control voltages $V_A$ or $V_B$ is changed slightly relative to the condition $V_B = -V_A$ applicable for an ideal system until the output signal of the lock-in amplifier 13 supplies an average $\Delta I_\perp$ which is sufficiently close to zero.

In the embodiment form shown in FIG. 4, the calibration of the measurement sensitivity is particularly simple. With the measurement sample 4 removed from the beam path ($\Gamma = 0$), the quantity $K' = I_\perp/(I_\perp + I_\parallel)$ is formed from the output signals of the lock-in detector 16, where $K' = \sin^2 \Lambda \sin^2 2\rho$ because $\Gamma = 0$. In the embodiment form according to FIG. 4, $\rho = 45°$, so that the quantity $K = \sin 2\Lambda \sin 2\rho = \sin 2\Lambda$ introduced above can easily be determined from $K' = \sin^2 \Lambda$.

Figure 6:
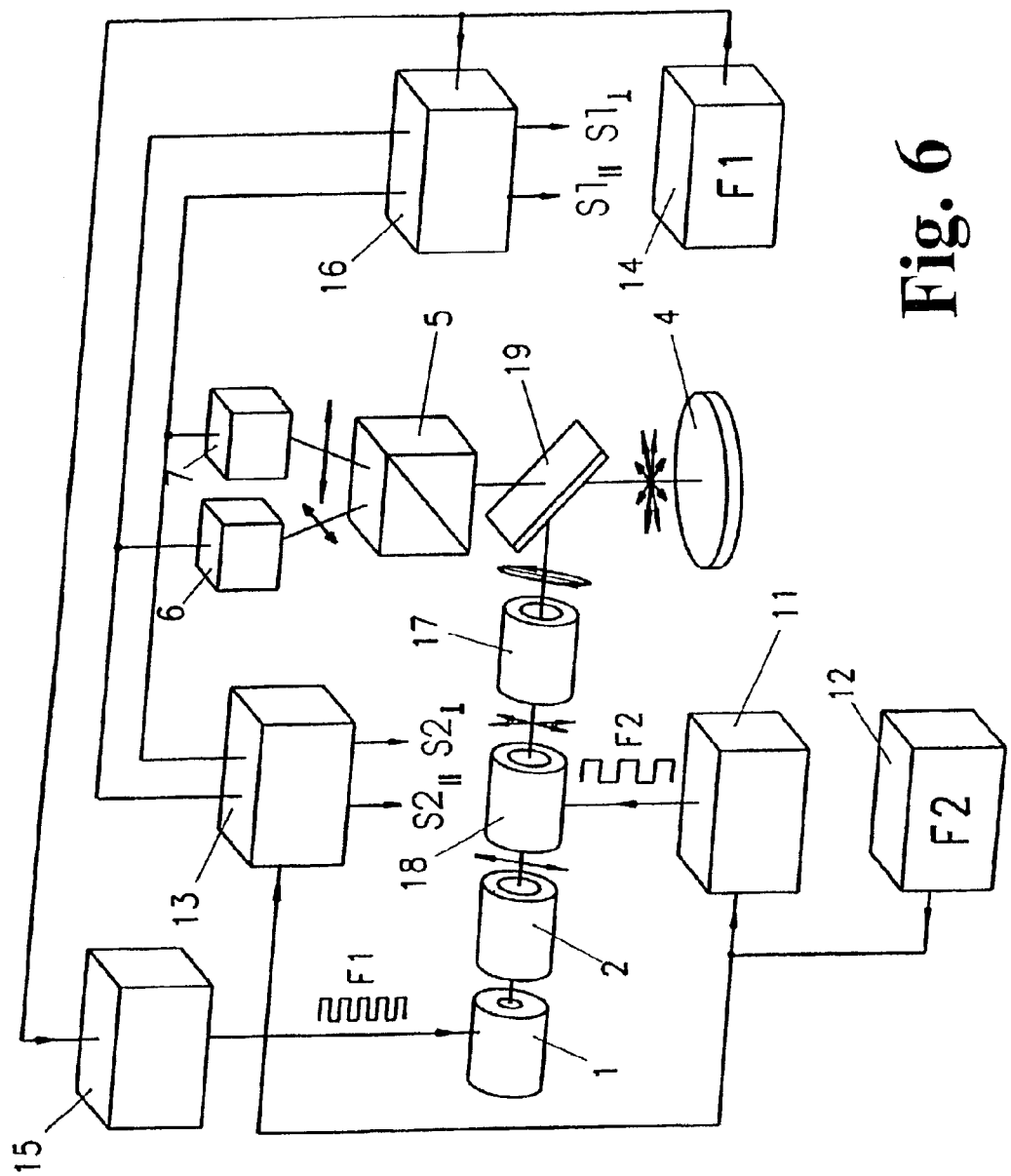
FIG. 6 shows the invention implemented in a reflection arrangement with an additional optical splitter 19, but otherwise with the same signal recording as in the transmission method shown in FIG. 4.

FIG. 6 illustrates the possibility of implementing the inventive solution mentioned above as a reflection arrangement, for which purpose an additional beam splitter 19 is introduced in the form of a partially transparent mirror 19. The latter deflects the elliptically polarized light onto the measurement sample 4. The portion of intensity reflected on the latter then passes through the partially transparent mirror 19 again into the polarizing splitter 5 acting as analyzer. The optical phase modulation is carried out and the signal is obtained in a manner analogous to FIG. 4.

While the foregoing description and drawings represent the present invention, it will be obvious to those skilled in the art that various changes may be made therein without departing from the true spirit and scope of the present invention.

What is claimed is:

1. A method for optical stress analysis comprising the steps of:

directing an incident beam of polarized light to a sample to be analyzed and analyzing a light bundle exiting the sample in two detection channels arranged perpendicular to one another with respect to the polarization direction;

providing that the incident beam is elliptically polarized;

carrying out the elliptical polarization with an elliptic shape having a comparatively large ratio of the large principal axis to the small principal axis;

the direction of rotation of the elliptical polarization of the incident beam changing periodically and using two alternative states of the direction of rotation for each measurement process;

adjusting the detection channels which extend perpendicular to one another corresponding to the position of the principal axes of the ellipse; and evaluating the difference between two measurements consecutively with the same beam intensity of the incident beam and the same ratio of principal axes, but with opposite directions of rotation of the elliptical polarization, being given by the two detection channels.

2. The method according to claim 1, wherein the elliptical polarization is generated in that the beam impinging on the sample is linearly polarized, its linear polarization being oriented, on the one hand, parallel to and, on the other hand, perpendicular to the two detection channels and after the object, passed through a birefringent phase retardation plate, wherein the ratio of the principal axes and the direction of rotation of the elliptical polarization are adjusted by the mutual orientation of the spatial position of the linear polarization to the principal axes of the phase retardation plate.

3. The method according to claim 2, wherein, in the measurements used for giving the difference, the angular position of the fast principal axis of the retardation plate changes in such a way that the direction of rotation of the elliptical polarization reverses while the ratio of the principal axes of the elliptical polarization remains unchanged.

4. The method according to claim 1, wherein the elliptical polarization is generated in that the incident beam is linearly polarized before the sample and then passing a controllable phase modulator, wherein the ratio of principal axes and the direction of rotation of the elliptical polarization are adjusted by control signals of the phase modulator.

5. The method according to claim 4, wherein the control signals of the phase modulator are periodically modulated in such a way that an elliptical polarization occurs with periodically changing direction of rotation, and the subtraction of successive measurements is carried out by a lock-in detector which is synchronously clocked by the control signal of the phase modulator.

6. The method according to claim 4, wherein the linearly polarized beam is generated by a laser.

7. The method according to claim 1, wherein the beam incident on the sample is modulated in intensity and the measurement values are detected by a lock-in detector.

8. An arrangement for optical stress analysis of materials based on stress induced birefringence comprising:

a light source being provided for generating a polarized beam incident on a sample to be analyzed;

a polarizing splitter being provided for dividing a light bundle exiting from the sample into two light receivers for detecting polarization directions perpendicular to one another;

an optical unit generating elliptically polarized light with adjustable ratio of the principal axes of the elliptical polarization being arranged in front of the sample;

direction of rotation of the elliptical polarization being adjustable in opposite directions with the ratio of the principal axes remaining constant;

said polarizing splitter acting as analyzer being oriented corresponding to the position of the principal axes of the ellipse for the polarization directions extending perpendicular to one another;

an electronic control unit being provided for synchronizing and allocating the intensity values of the two light receivers to the states of elliptical polarization that are adjusted by the optical unit; and a processing unit being provided for evaluating the intensity values of the two light receivers for two associated states with opposite directions of rotation of the elliptical polarization, intensity values of the one light receiver which are measured for associated states being subtracted and the difference being normalized to the sum of the intensity values of both light receivers for both associated states.

9. The arrangement according to claim 8, wherein the optical unit for adjusting two states of opposite directions of rotation of the elliptical polarization is a controllable optical phase shifter (retarder) which is arranged in the optical light path between the light source and the sample.

10. The arrangement according to claim 9, wherein the optical unit for adjusting two states of opposite directions of rotation of the elliptical polarization is a mechanically controlled retarder, wherein the retarder has a changeable angular position.

11. The arrangement according to claim 8, wherein the optical unit for adjusting two states of opposite directions of rotation of the elliptical polarization is an electronically controllable phase modulator which has an alternating phase shift.

12. The arrangement according to claim 11, wherein the optical unit is an electro-optical phase modulator, wherein the phase shift is adjustable by changing the control voltage or the control current.

13. The arrangement according to claim 11, wherein the optical unit is a magneto-optical phase modulator, wherein the phase shift is adjustable by changing the control voltage or the control current.

14. The method according to claim 1, wherein the elliptical polarization is generated in that the beam for analyzing the object is linearly polarized, its linear polarization being orientated, on the one hand, parallel to and, on the other hand, perpendicular to the two detection channels and before striking the object, passed through a birefringent phase retardation plate, wherein the ratio of the principal axes and the rotating direction of the elliptical polarization are adjusted by the mutual orientation of the spatial position of the linear polarization to the principal axes of the phase retardation plate.

15. The method according to claim 1, wherein the elliptical polarization is generated in that the incident beam is linearly polarized and passing a controllable phase modulator before the object, wherein the ratio of the principle axes and the rotating direction of the elliptical polarization are adjusted by control signals of the phase modulator.

* * * * *